(12) United States Patent
Adie et al.

(10) Patent No.: US 7,881,509 B2
(45) Date of Patent: Feb. 1, 2011

(54) METHOD OF, AND APPARATUS AND COMPUTER SOFTWARE FOR, IMAGING BIOLOGICAL OBJECTS

(75) Inventors: Elaine J. Adie, South Wales (GB); Nicholas S. Arini, Botley (GB)

(73) Assignee: GE Healthcare UK Limited, Amersham (GB)

( * ) Notice: Subject to any disclaimer, the term of this patent is extended or adjusted under 35 U.S.C. 154(b) by 845 days.

(21) Appl. No.: 11/721,185

(22) PCT Filed: Dec. 9, 2005

(86) PCT No.: PCT/GB2005/004747
§ 371 (c)(1),
(2), (4) Date: Jun. 8, 2007

(87) PCT Pub. No.: WO2006/061640
PCT Pub. Date: Jun. 15, 2006

(65) Prior Publication Data
US 2009/0232370 A1    Sep. 17, 2009

(30) Foreign Application Priority Data
Dec. 10, 2004    (GB) .................................. 0427050.0

(51) Int. Cl.
*G06K 9/00* (2006.01)
*G02B 26/08* (2006.01)

(52) U.S. Cl. ...................... 382/128; 382/274; 359/210.1

(58) Field of Classification Search ................. 382/128, 382/129, 130, 131, 132, 133, 134, 168, 181, 382/191, 214, 219, 232, 254–257, 274, 276, 382/305, 312; 359/210.1, 196.1; 424/9.8; 435/5, 7.21; 702/19
See application file for complete search history.

(56) References Cited

U.S. PATENT DOCUMENTS

| | | | | |
|---|---|---|---|---|
| 6,090,541 A | * | 7/2000 | Wicks et al. | 435/5 |
| 6,187,289 B1 | * | 2/2001 | Richards-Kortum et al. | 424/9.8 |
| 6,388,788 B1 | * | 5/2002 | Harris et al. | 359/196.1 |
| 6,400,487 B1 | * | 6/2002 | Harris et al. | 359/210.1 |
| 2003/0036855 A1 | * | 2/2003 | Harris et al. | 702/19 |
| 2003/0096322 A1 | * | 5/2003 | Giuliano et al. | 435/7.21 |

FOREIGN PATENT DOCUMENTS

EP    1 219 950    5/2005
WO    WO 01/17567    3/2001

* cited by examiner

*Primary Examiner*—Seyed Azarian
(74) *Attorney, Agent, or Firm*—Yonggang Ji (57) ABSTRACT

A method of imaging one or more biological objects using imaging apparatus capable of capturing an image across an imaging area. The method includes: placing the one or more biological objects (236) in an environment; providing in the environment, outside of the one or more biological objects, a contrast enhancing agent which provides contrast in an image between the one or more biological objects and the environment; and recording an image (240) of the one or more biological objects and the environment using the imaging apparatus, whereby a spatial definition for said one or more biological objects is derivable using contrast in the image which is provided by the contrast enhancing agent.

23 Claims, 11 Drawing Sheets

METHOD OF, AND APPARATUS AND COMPUTER SOFTWARE FOR, IMAGING BIOLOGICAL OBJECTS

CROSS-REFERENCE TO RELATED APPLICATIONS

This application is a filing under 35 U.S.C. §371 and claims priority to international patent application number PCT/GB2005/004747 filed Dec. 9, 2005, published on Jun. 15, 2006, as WO 2006/061640, which claims priority to patent application number 0427050.0 filed in Great Britain on Dec. 10, 2004; the disclosures of which are incorporated herein by reference in their entireties.

FIELD OF THE INVENTION

The invention relates to a method of imaging one or more biological objects using imaging apparatus. The invention further relates to computer software and apparatus arranged to perform such a method.

BACKGROUND OF THE INVENTION

There is currently a need in drug discovery and development and in general biological research for methods and apparatus for accurately performing cell-based assays. Cell-based assays are advantageously employed for assessing the biological activity of chemical compounds.

In addition, there is a need to quickly and inexpensively screen large numbers of chemical compounds. This need has arisen in the pharmaceutical industry where it is common to test chemical compounds for activity against a variety of biochemical targets, for example, receptors, enzymes and nucleic acids. These chemical compounds are collected in large libraries, sometimes exceeding one million distinct compounds.

Performing cell-based assays often involves recording cellular images and quantifying these images using algorithms of image analysis software. Instruments are known for imaging fluorescently labelled cells and software of these instruments have a number of analysis modules which quantify, for example, biological protein translocations and reactions to stimuli within the fluorescently labelled cells.

Analysing such cellular images involves identifying regions of the image corresponding to the cells and this is generally achieved by detecting fluorescent radiation emitted by a fluorescently labelled cell. One example of such a label is a marker stain which labels the cell nucleus, for example HOECHST 33342™ manufactured by Invitrogen, or DRAQ5™ manufactured by Biostatus.

In order to label the cell nucleus, these nuclear stains interact with the nucleic acid structure of the nucleus. This interaction, over a period of time, proves to be toxic to the cell. It is important that data collected when performing cell-based assays is as accurate as possible and the toxicity of nuclear stains therefore prevents their use in live cell assays where it is desired to mark and measure cell responses at intervals over a relatively long time period.

Marking cell organelles other than the nucleus is often difficult. Markers for the cytosol, plasma membrane or Golgi apparatus are not effective over a relatively long period of time as they degrade or relocalise within the cell over time.

The use of contrast agents in imaging of biological objects is known in the art.

U.S. Pat. No. 6,187,289 discloses the use of acetic acid as a contrast agent in reflectance confocal imaging of cells.

Methods employing contrast-coloring dyes in combination with precipitable dyes have been reported in U.S. Pat. No. 6,090,541 to enhance the visualization of bacteriophage-derived plaques in confluent lawns of bacteria. The contrast-coloring dyes are capable of coloring the support material while the precipitable dyes serve as a substrate for a bacterial or viral enzyme to produce a colored precipitate.

Metal complex contrast agents are known for MRI and X-ray imaging, as disclosed in WO 01/17567.

It is an object of the invention to provide an improved method of imaging biological objects during a biological assay.

SUMMARY OF THE INVENTION

In accordance with a first aspect of the present invention, there is provided a method of imaging one or more biological objects using imaging apparatus capable of capturing an image across an imaging area, said method including:

a) placing said one or more biological objects in an environment;

b) providing in said environment, outside of said one or more biological objects, a contrast enhancing agent which provides contrast in an image between said one or more biological objects and said environment; and c) recording an image of said one or more biological objects and said environment using said imaging apparatus, whereby a spatial definition for said one or more biological objects is derivable using contrast in said image which is provided by said contrast enhancing agent.

The present invention allows relatively accurate spatial definition data of biological objects to be obtained from assays of biological objects performed over relatively long time periods. By providing the contrast enhancing agent in the environment outside the biological objects, it is not necessary to introduce toxic compounds into the biological objects in order to identify the objects' location in the image and consequently a deterioration of the objects' health during the assay is minimised.

In preferred embodiments of the present invention, said contrast enhancing agent is provided in a medium in which said one or more biological objects are supported.

In different preferred embodiments of the present invention the method comprises providing a medium in which said one or more biological objects are supported and providing said contrast enhancing agent in a region outside of said medium.

The medium provides nutrients and living conditions which maintain the health of the biological objects. In the preferred embodiments where the contrast enhancing agent is the medium, providing the medium provides the contrast in the image in a relatively simple manner. In other preferred embodiments, situating the contrast enhancing agent outside of the medium allows the contrast enhancing agent to be provided separately to the medium. This allows assays to be performed in accordance with the invention where it is undesirable to use a medium which comprises the contrast enhancing agent.

The method preferably comprises providing a receptacle containing said one or more biological objects, wherein at least part of said receptacle is formed of said contrast enhancing agent.

The receptacle is provided separately to the medium and can provide the contrast in the image between the biological objects and the environment. These receptacles may have standard dimensions and a standard background fluorescence and, when used in assays performed in accordance with the invention, they ensure that assay conditions are consistent.

In further preferred embodiments, the method comprises providing a receptacle containing said one or more biological objects, wherein an inside surface of said receptacle includes a coating which includes a layer of said contrast enhancing agent.

Receptacles which are not formed of the contrast enhancing agent and which have various dimensions and configurations, and which are produced by different manufacturers, can be used in accordance with the invention. By providing the coating to the inside surface of such receptacles, the contrast in the image between the biological objects and the environment is provided in the image.

Preferably the method comprises rendering said coating adhesive, such that said one or more biological objects adhere to a surface of said coating.

Biological objects adhered to the coating are kept in contact with the coating, thus allowing relatively accurate assays to be performed. The adhesion may aid formation of a layer of the biological objects within the environment which has a thickness of one biological object and may keep the objects within an imaging plane of the imaging apparatus.

In preferred embodiments of the present invention, said method includes:

i) applying a brightness threshold to said image in order to identify relatively dark pixels and relatively light pixels, so as to produce a thresholded image;

ii) segmenting said thresholded image into object areas.

Thresholding the recorded image uses the contrast provided by the contrast enhancing agent to identify pixels in the image which may correspond to the biological objects and to the environment. Segmentation identifies areas of the thresholded image which correspond to the biological objects. These object areas may be used to derive spatial definitions for the objects.

In preferred embodiments said one or more biological objects include one or more components within said one or more objects and said method comprises marking said components with a second contrast enhancing agent which provides contrast in an image between said components and other areas of said one or more biological objects.

Using the second contrast enhancing agent a spatial definition of components of the biological objects may additionally be derived. The biological objects may be cells and in such cases the components are sub-cellular components.

Preferably said contrast enhancing agent is non-toxic to said one or more biological objects.

A non-toxic contrast enhancing agent minimises a deterioration of the health of the biological objects so that a relatively accurate spatial definition for the objects can be derived for assays performed over a relatively long period of time.

The invention also provides, in a further aspect, apparatus arranged to perform the above method.

In accordance with a further aspect of the present invention, there is provided computer software for use in analysing one or more biological objects generated using imaging apparatus by capturing an image across an imaging area, said image being captured by:

a) placing said one or more biological objects in an environment;

b) providing in said environment, outside of said one or more biological objects, a contrast enhancing agent which provides contrast in an image between said one or more biological objects and said environment; and c) recording an image of said one or more biological objects and said environment using said imaging apparatus, wherein said software is arranged to derive a spatial definition for said one or more biological objects using contrast in said image which is provided by said contrast enhancing agent.

In accordance with yet further aspects of the present invention, there is provided a contrast enhancing agent for use in an environment outside of one or more biological objects to be imaged and a receptacle for containing one or more biological objects in an environment.

Further features and advantages of the invention will become apparent from the following description of preferred embodiments of the invention, given by way of example only, which is made with reference to the accompanying drawings.

DETAILED DESCRIPTION OF THE INVENTION

The present invention provides a method of imaging one or more biological objects using imaging apparatus capable of capturing an image across an imaging area. The imaging apparatus comprises an imaging system having image analysis computer software which includes functionality such that a spatial definition for one or more of the biological objects is derivable. Embodiments of the present invention will be described below in which the biological objects are cells.

Imaging System

Figure 1:
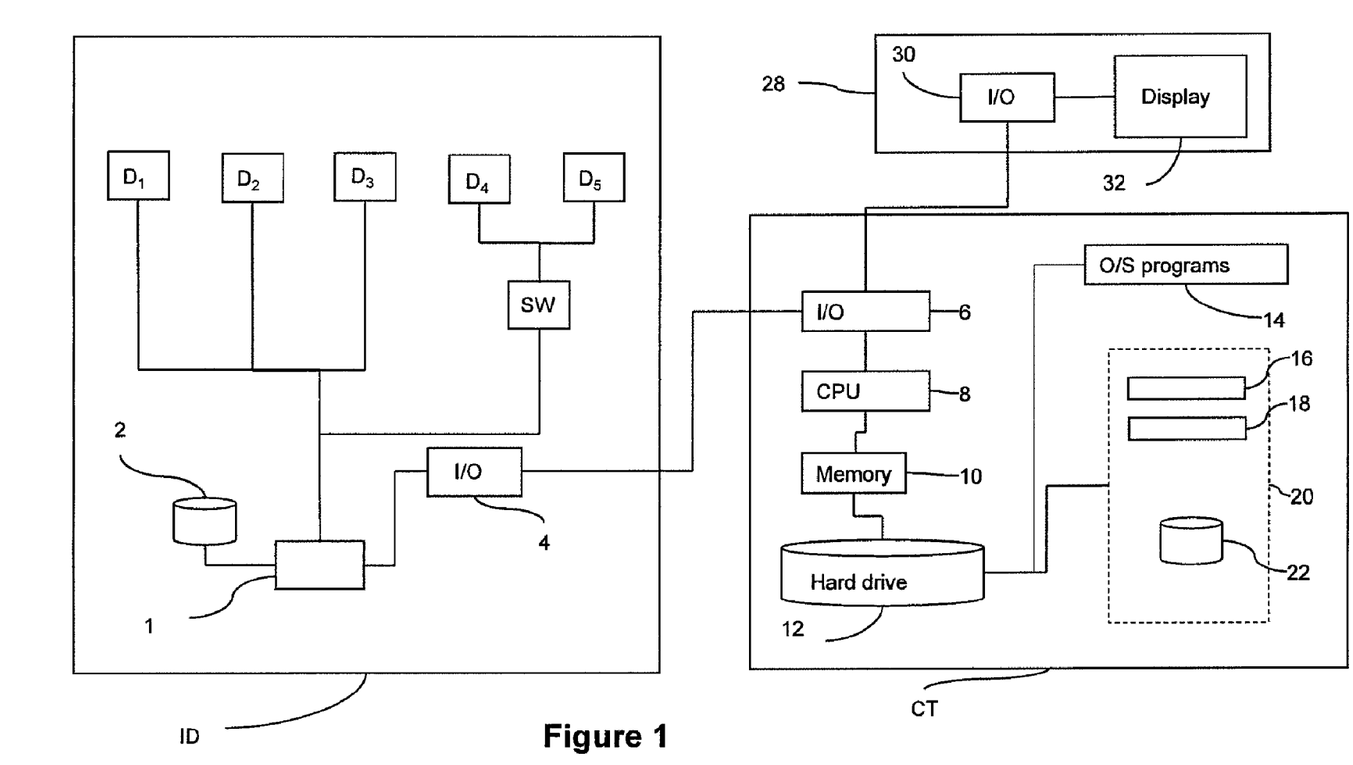
FIG. 1 is a schematic illustration showing data processing components in an imaging system arranged in accordance with an embodiment of the invention.

The imaging system will be described with reference to FIG. 1 which shows a schematic illustration of data processing components of an imaging system arranged in accordance with the invention. The system includes an imaging device ID, such as a confocal microscope, as described in further detail below, which includes detectors $D_1$, $D_2$, $D_3$, $D_4$, $D_5$, a switch SW, a control unit 1, an image data store 2 and an Input/Output (I/O) device 4. An associated computer terminal CT includes a central processing unit (CPU) 8, memory 10, a data storage device such as a hard disc drive 12 and I/O devices 6 which facilitate interconnection of the computer CT with both the imaging device ID via the I/O device 4, and a display element 32 of a screen 28 via a screen I/O device 30. Operating system programs 14 are stored on the hard disc drive 12 and control, in a known manner, low level operation of the computer terminal CT. Program files and data 20 are also stored on the hard disc drive 12, and control, in a known manner, outputs to an operator via associated devices and output data stored on the hard disc drive 12. The associated devices include the display 32 as an element of the screen 28, a pointing device (not shown) and keyboard (not shown), which receive input from, and output information to, the operator via further I/O devices (not shown). Included in the program files 20 stored on the hard drive 12 are an assay control application 16, an image processing and analysis software system 18, and a database 22 for storing image data received from the imaging device ID and output files produced during data processing. The image analysis software system 18 may be a customized version of known image processing and analysis software packages.

The performance of an assay using the imaging device ID is controlled using control application 16, and the image data are acquired. After the end of acquisition of image data for at least one well in a multi-well plate by at least one detector $D_1$, $D_2$, $D_3$, the image data are transmitted to the computer terminal CT and stored in the database 22 on the computer terminal hard drive 12, at which point the image data can be processed using the image processing and analysis software system 18, as will be described in greater detail below.

Figure 2:
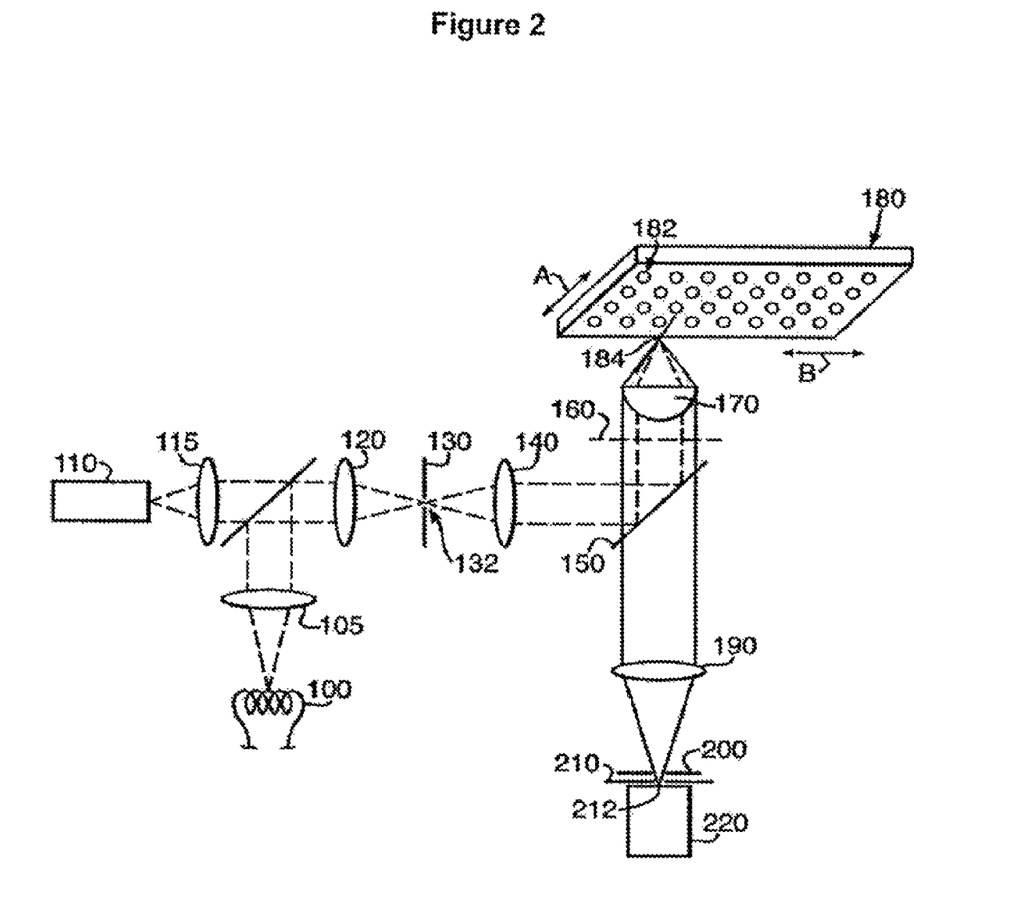
FIG. 2 is a schematic view of a first embodiment of a line-scan confocal microscope used to image samples according to the present invention.

FIG. 2 shows an embodiment of the present invention, where the imaging device ID used is a confocal microscope based on the Amersham Biosciences IN CELL ANALYZER™ system as described in U.S. Pat. Nos. 6,400,487 and 6,388,788 and co-pending U.S. patent application publication number US2003-0036855. The microscope comprises a source 100 or 110 of electromagnetic radiation for example, in the optical range, 350-750 nm, a cylindrical lens 120, a first slit mask 130, a first relay lens 140, a dichroic mirror 150, an objective lens 170, a multi-well plate 180 containing a two-dimensional array of sample wells 182, a tube lens 190, a filter 200, a second slit mask 210 and a detector 220. These elements are arranged along optical axis OA with slit apertures 132, 212 in masks 130, 210 extending perpendicular to the plane of FIG. 2. The focal lengths of lenses 140, 170 and 190 and the spacings between these lenses as well as the spacings between mask 130 and lens 140, between objective lens 170 and multi-well plate 180 and between lens 190 and mask 210 are such as to provide a confocal microscope. In this embodiment, electromagnetic radiation from a lamp 100 or a laser 110 is focused to a line using a cylindrical lens 120. The shape of the line is optimized by a first slit mask 130. The slit mask 130 is depicted in an image plane of the optical system that is in a plane conjugate to the object plane. The illumination stripe formed by the aperture 132 in the slit mask 130 is relayed by lens 140, dichroic mirror 150 and objective lens 170 onto a multi-well plate 180 which contains a two-dimensional array of sample wells 182. For convenience of illustration, the optical elements of FIG. 2 are depicted in cross-section and the multi-well plate in perspective. The projection of the line of illumination onto multi-well plate 180 is depicted by line 184 and is also understood to be perpendicular to the plane of FIG. 2. As indicated by arrows A and B, multi-well plate 180 may be moved in two dimensions (X, Y) parallel to the dimensions of the array by means not shown.

An image of the sample area, for example a sample in a sample well 182, is obtained by projecting the line of illumination onto a plane within the sample, imaging the fluorescence emission therefrom onto a detector 220 and moving the plate 180 in a direction perpendicular to the line of illumination, synchronously with the reading of the detector 220. In the embodiment depicted in FIG. 2, the fluorescence emission is collected by the objective lens 170, projected through the dichroic beamsplitter 150, and imaged by lens 190 through filters 200 and a second slit mask 210 onto a detector 220, such as is appropriate to a confocal imaging system having an infinity-corrected objective lens 170. The dichroic beamsplitter 150 and filter 200 preferentially block light at the illumination wavelength. The detector 220 illustratively is a camera and may be either one dimensional or two dimensional. If a one dimensional detector is used, slit mask 210 is not needed. The illumination, detection and translation procedures are continued until the prescribed area has been imaged.

An embodiment enabling multi-wavelength fluorescence imaging is preferred for certain types of assays. In this way, image data can be generated for the same area being imaged in each of a plurality of different color channels simultaneously.

Figure 3A:
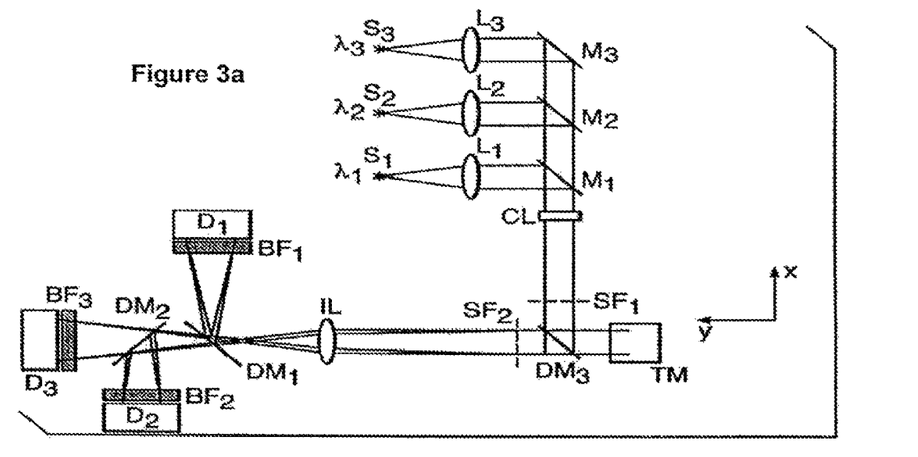
FIGS. 3A and 3B are, respectively, a top view and a side view of the ray path of a multicolor embodiment of the present invention, without a scanning mirror.
Figure 3B:
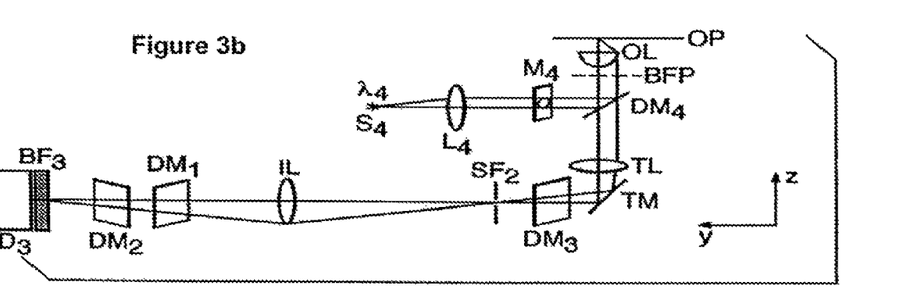
Figure 3C:
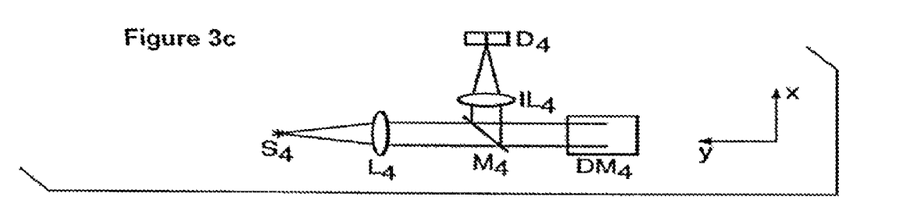
FIG. 3C is a top view of the ray path of a single beam autofocus.

The number of independent wavelengths or colors will depend on the specific assay being performed. In one embodiment three illumination wavelengths are used. FIGS. 3A and 3B depict the ray paths in a three-color line-scan confocal imaging system, from a top view and a side view respectively. In general, the system comprises several sources $S_n$ of electromagnetic radiation, collimating lenses $L_n$, and mirrors $M_n$ for producing a collimated beam that is focused by cylindrical lens CL into an elongated beam at first spatial filter $SF_1$, a confocal microscope between first spatial filter $SF_1$, and second spatial filter $SF_2$ and an imaging lens IL, beamsplitters $DM_1$ and $DM_2$ and detectors $D_n$ for separating and detecting the different wavelength components of fluorescent radiation from the sample. Spatial filters SF, and $SF_1$ and $SF_2$ preferably are slit masks.

In particular, FIG. 3A depicts sources, $S_1$, $S_2$ and $S_3$, for colours $\lambda_1$, $\lambda_2$ and $\lambda_3$, and lenses $L_1$, $L_2$ and $L_3$ that collimate the light from the respective sources. Lenses $L_1$, $L_2$ and $L_3$, preferably are adjusted to compensate for any chromaticity of the other lenses in the system. Mirrors $M_1$, $M_2$ and $M_3$ are used to combine the illumination colors from sources $S_n$. The mirrors $M_2$ and $M_1$ are partially transmitting, partially reflecting and preferentially dichroic. $M_2$, for example, should preferentially transmit $\lambda_3$, and preferentially reflect $\lambda_2$. It is thus preferential that $\lambda_3$ be greater than $\lambda_2$.

Operation of the microscope in a confocal mode requires that the combined excitation beams from sources $S_n$ be focused to a "line", or a highly eccentric ellipse, in the object plane OP. As discussed in connection to FIG. 2 above, a variety of configurations may be used to accomplish this. In the embodiment depicted in FIG. 3A, the combined illumination beams are focused by cylindrical lens CL into an elongated ellipse that is coincident with the slit in the spatial filter $SF_1$. As drawn in FIGS. 3A and 3B, the slit mask $SF_1$ resides in an image plane of the system, aligned perpendicular to the propagation of the illumination light and with its long axis in the plane of the page of FIG. 3A. The lenses TL and OL relay the illumination line from the plane containing $SF_1$ to the object plane OP. A turning mirror, TM, is for convenience. In another embodiment, $DM_3$ is between TL and OL and CL focuses the illumination light directly into the BFP. Other embodiments will be evident to one skilled in the art.

Referring to FIG. 3B, the light emitted by the sample and collected by the objective lens, OL, is imaged by the tube lens, TL, onto the spatial filter, $SF_2$. $SF_2$ is preferentially a slit aligned so as to extend perpendicular to the plane of the page. Thus, the light passed by filter $SF_2$ is substantially a line of illumination. $SF_2$ may be placed in the primary image plane or any plane conjugate thereto. $DM_3$ is partially reflecting, partially transmitting and preferably "multichroic". Multi-wavelength "dichroic" mirrors or "multichroic" mirrors can be provided that preferentially reflect certain wavelength bands and preferentially transmit others.

Here, $\delta\lambda_1$ will be defined to be the fluorescence emission excited by $\lambda_1$. This will, in general, be a distribution of wavelengths somewhat longer than $\lambda_1$. $\delta\lambda_2$ and $\delta\lambda_3$ are defined analogously. $DM_3$ preferentially reflects $\lambda_n$, and preferentially transmits $\delta\lambda_n$, n=1, 2, 3. The light transmitted by $SF_2$ is imaged onto the detection devices, which reside in planes conjugate to the primary image plane. In FIG. 3A, an image of the spatial filter $SF_2$ is created by lens IL on all three detectors, $D_n$. This embodiment is preferred in applications requiring near-perfect registry between the images generated by the respective detectors. In another embodiment, individual lenses $IL_n$ are associated with the detection devices, the lens pairs IL and $IL_n$ serving to relay the image of the spatial filter $SF_2$ onto the respective detectors $D_n$. The light is split among the detectors by mirrors $DM_1$ and $DM_2$. The mirrors are partially transmitting, partially reflecting, and preferentially dichroic. $DM_1$ preferentially reflects $\delta\lambda_1$ and preferentially transmits $\delta\lambda_2$ and $\delta\lambda_3$. The blocking filter, $BF_1$, preferentially transmits $\delta\lambda_1$ effectively blocking all other wavelengths present. $DM_2$ preferentially reflects $\delta\lambda_2$ and preferentially transmits $\delta\lambda_3$. The blocking filters, $BF_2$ and $BF_3$, preferentially transmit $\delta\lambda_2$ and $\delta\lambda_3$ respectively, effectively blocking all other wavelengths present.

Image Acquisition

Images can be recorded of a cellular assay using the imaging system. A sample cell culture may be placed in a plurality of receptacles, in this example sample wells of a multi-well microtitre plate, different chemical compounds placed in each well, and, at a desired time following the addition of the chemical compounds, image acquisition can be performed of the samples.

Figures 4, 5:
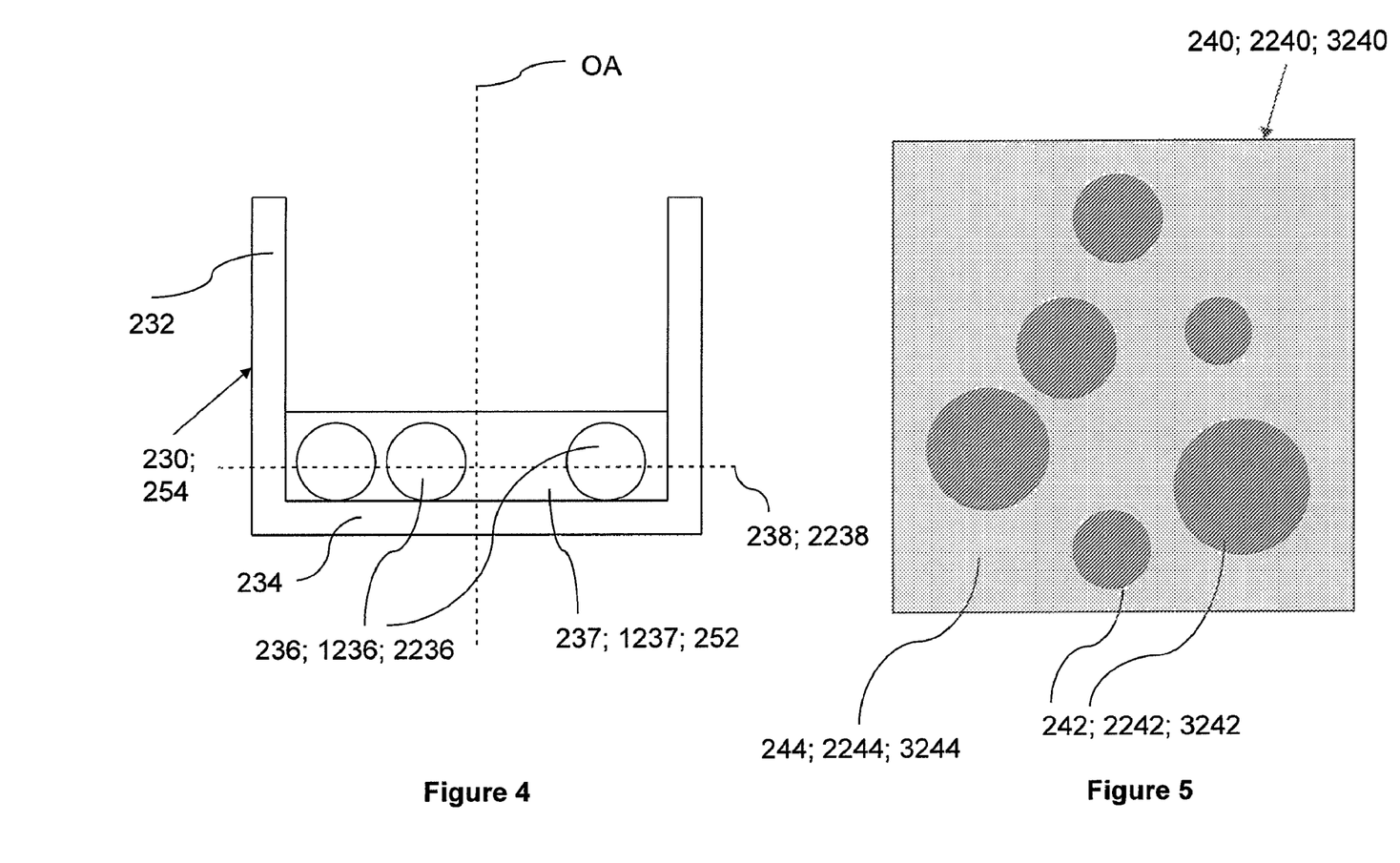
FIG. 4 shows a cross section of a receptacle containing biological objects in accordance with embodiments of the present invention.
FIG. 5 shows schematically an image of biological objects in accordance with embodiments of the present invention.

FIG. 4 shows in cross section a sample well 230 for imaging in accordance with an embodiment of the invention and which contains a cell culture. The sample well 230 is similar to the sample well 182 described previously and is located on the optical axis OA of the imaging system. The well 230 has a cylindrical wall 232 integrally formed with a base plate 234 which covers one end of the cylindrical wall such that the well 230 has a U-shaped cross section. The well 230 provides an environment to cells 236 of the cell culture. The cells 236 are placed into the environment by placing the cells 236 inside the well 230 onto the base plate 234. The cells 236 are distributed in a material located outside of the cells 236 which contains a predetermined concentration of a contrast enhancing agent (CEA) which is distributed approximately homogeneously throughout the material. The material is a medium 237 which is non-toxic to the cells 236, which supports the cells 236 by providing nutrients and conditions which maintain a health of the cells 236 and which helps the cell culture to grow. The cells 236 form a layer across the base plate 234 which has a thickness of approximately one cell. In further embodiments, the layer may have a thickness which is greater than one cell.

In this embodiment the CEA is arranged to emit fluorescent radiation of a predetermined wavelength during imaging. The concentration of the CEA is selected such that a predetermined amount of this radiation is emitted. The confocal microscope described previously records an image of the cells 236 and the environment across an imaging area of the sample. The imaging area lies in a plane 238 which is perpendicular the optical axis OA and which passes through the layer of cells 236. The confocal microscope records the image in a first channel by detecting the predetermined wavelength of the fluorescent radiation emitted by the medium 237. Areas of the imaging area which are occupied by the cells 236 may be irradiated by the radiation emitted by the CEA. Settings of the confocal microscope may be adjusted and the concentration of the CEA in the medium 237 may be selected in order to account for this irradiation, so that a high quality image is recorded.

FIG. 5 shows schematically an image 240 recorded in accordance with this embodiment. The CEA provides a contrast in the image 240 between relatively dark areas 242 of the image corresponding to positions of the cells 236 in the imaging area, and relatively light areas 244 of the image corresponding to the environment.

Figure 6:
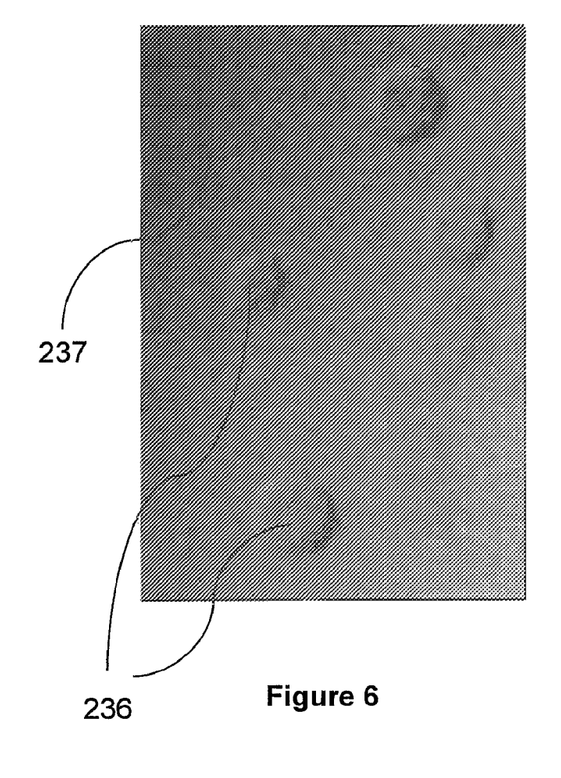
FIGS. 6 and 7 show exemplary images of biological objects recorded in accordance with one embodiment of the present invention.
Figure 7:
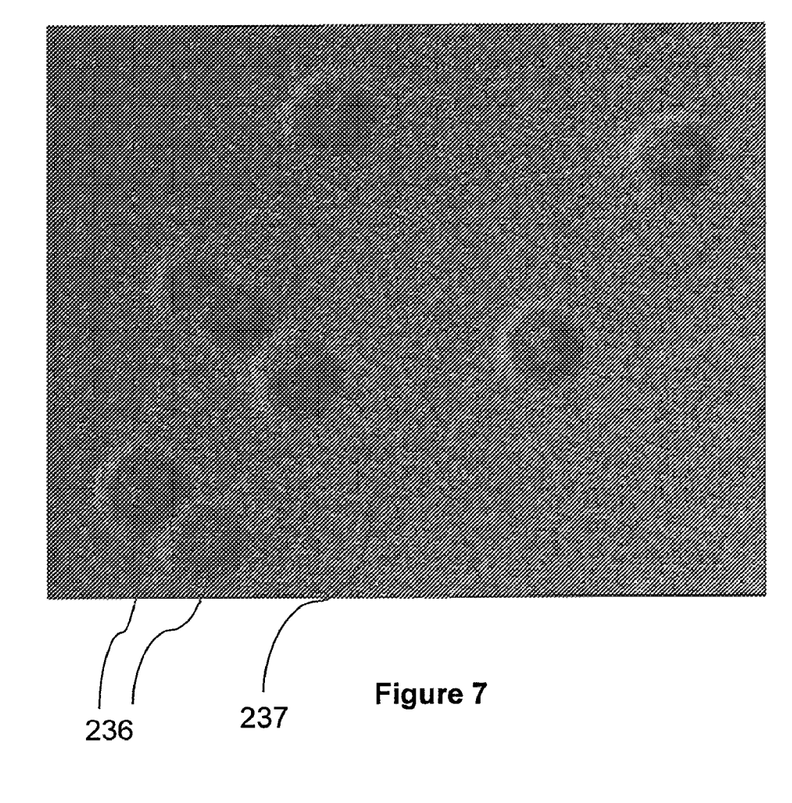

FIGS. 6 and 7 show examples of images recorded in accordance with this embodiment. In this example the cells 236 are Hela cells and the medium 237 is a CYDYE™ (GE Healthcare Bio-Sciences, UK) derivative compound in which the cells 236 have been incubated. The medium 237 is excluded by the cells 236.

Figure 8:
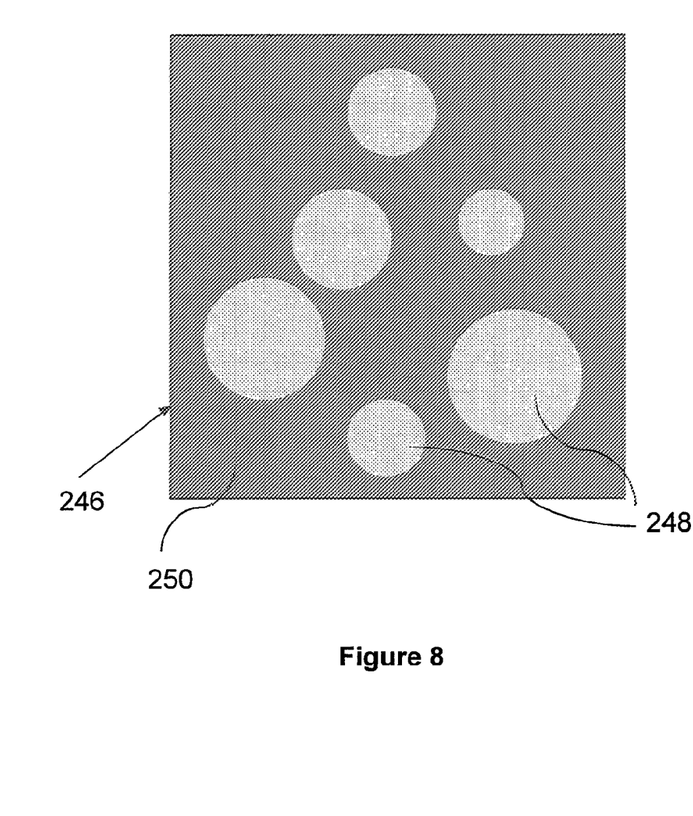
FIG. 8 shows schematically an image of biological objects in accordance with an embodiment of the present invention.

A different embodiment of the present invention will now be described with reference to FIG. 4 and FIG. 8. Features and elements of this embodiment are similar to features described in the previous embodiment and are referred to using the same reference numerals, incremented by 1000. Corresponding descriptions should be taken to apply here also. Rather than the confocal microscope described in the previous embodiment, the imaging system in this embodiment is a transmission microscope, which transmits radiation through the environment, and therefore through the imaging area, and detects the transmitted radiation in order to record the image of the cells and the environment. The transmitted radiation has, in this example, a wavelength lying in the visible light region of the electromagnetic spectrum, although the wavelength may in different embodiments alternatively lie in a different region of the electromagnetic spectrum, for example the ultra violet region. The transmission microscope may be of a brightfield type or a phase-contrast type.

In this embodiment the CEA is selected so that the medium 1237 has a transmissivity for the transmitted radiation which is lower than a transmissivity of the cells 1236 to the transmitted radiation. The CEA has a predetermined concentration in the material so that the medium 1237 is opaque to the transmitted radiation. The concentration of the CEA in different embodiments may be controlled in order to obtain a different level of opacity of the medium 1237 to the transmitted radiation. FIG. 8 shows schematically an image 246 recorded in accordance with this embodiment. The CEA provides a contrast in the image between relatively light areas 248 of the image corresponding to positions of the cells 1236 in the imaging area and relatively dark areas 250 corresponding to the environment.

A further embodiment of the present invention will now be described with reference to FIGS. 4 and 5. Features and elements of this embodiment are similar to features described in the previous embodiments and are referred to using the same reference numerals, incremented by 2000. Corresponding descriptions should be taken to apply here also.

In this embodiment the cells 2236 are distributed in a medium 252 which supports the cells 2236 by providing nutrients and conditions which maintain the health of the cells 2236 and which helps the cell culture to grow, but which does not comprise the CEA. The cells 2236 are placed in an environment in a sample well 254 of a microtitre plate which is similar to the sample well 230 described previously using FIG. 4, but which is formed of a material comprising the CEA. In this way the material is located in a region outside of the medium 252. In different embodiments only part of the sample well 254 may be formed of the material. Alternatively, the material may be embedded in parts of the sample well; or beads which are formed of the material, or which are coated in the material, may be embedded in parts of the sample well. The CEA emits fluorescent radiation during imaging and the imaging system in this embodiment is the confocal microscope described previously. A concentration of the CEA in the material is selected so that the fluorescent radiation emitted by the CEA radiates into the plane 2238 of the imaging area such that the CEA provides the contrast in the image 2240 between the cells 2236 and the environment. With reference to FIG. 5, the cells 2236 restrict, or alternatively prevent, the presence of the emitted radiation, which is available for detection by the confocal microscope, within areas lying in the plane 2238 which are occupied by the cells 2236. In this way, the relatively dark areas 2242 of the recorded image 2240 correspond to the cells 2236 and the relatively light areas 2244 correspond to the medium 252.

A further embodiment of the present invention will now be described with reference to FIGS. 5 and 9. Features and elements of this embodiment are similar to features described in the previous embodiment and are referred to using the same reference numerals, incremented by 3000. Corresponding descriptions should be taken to apply here also.

Figure 9:
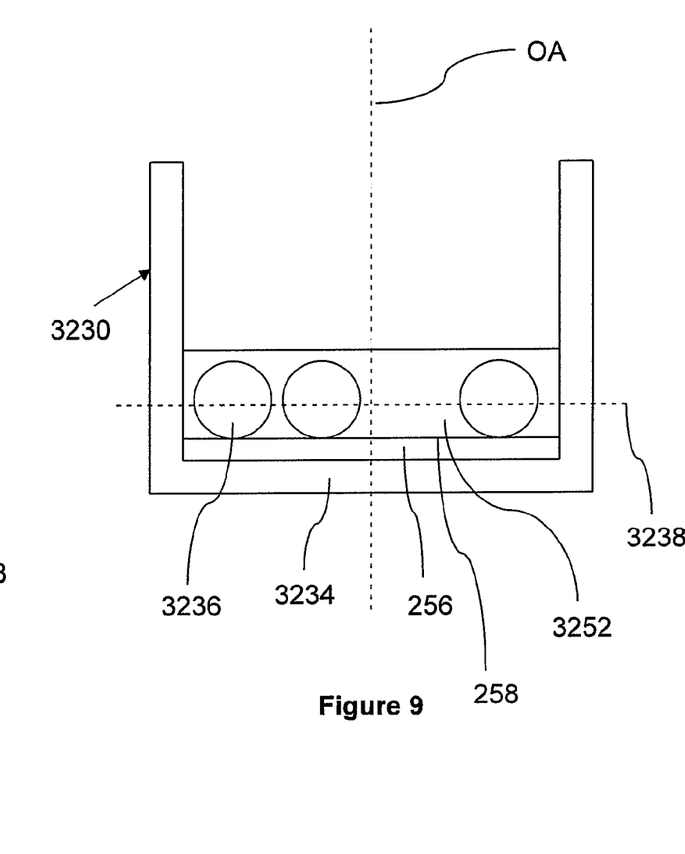
FIG. 9 shows, in cross section, a receptacle containing biological objects in accordance with an embodiment of the present invention.

Referring to FIG. 9, the sample well 3230 is not formed of the material and the medium 3252 does not comprise the material. An inside surface of the base plate 3234 includes a coating which includes a layer 256 of the material having a predetermined concentration of the CEA. The material is rendered adhesive so that the cells 3236 adhere to a surface 258 of the coating. This may aid the formation of the layer of cells 3236 having a one cell thickness. The material is, for example, a positively charged polymer such as polylysine, polyornithine, collagen, fibronectin, laminin or gelatin. The CEA is a fluorescent dye, for example a CYDYE™, which is used to label the material. For example, polylysine may be labelled with the fluorescent dye Cy5. A stability of the material having the CEA, in this example the CYDYE™ polymer conjugate, may be predetermined so that the conjugate does not decompose within a certain period of time, for example approximately 48 to 72 hours, when exposed to the cell culture. In different embodiments, the coating may comprise a plurality of different layers.

The concentration of the CEA is selected so that during imaging the CEA emits fluorescent radiation which radiates into the plane 3238 of the imaging area. The cells 3236 restrict, or alternatively prevent, the presence of the emitted radiation, which is available for detection by the confocal microscope, within areas of the imaging area which are occupied by the cells 3236. With reference to FIG. 5, the image 3240 is recorded with the confocal microscope and the CEA provides the contrast in the image between the relatively dark areas 3242 and the relatively light areas 3244.

In further embodiments of the present invention, one or more components within the biological objects, in this case cells, may be marked using a second CEA which provides contrast in a recorded image between the components and other areas of the cells. In this case the components are sub-cellular components, for example granules, Golgi apparatus, cell nuclei and cellular membranes of the cells. In the case of a cell nucleus, the second CEA may be a nuclear marker such as one of the toxic intercalating nuclear dyes (such as DRAQ5™ or a HOECHST™ dye, for example Hoechst 33342). Alternatively, non-toxic markers such as an NLS-fluorescent protein fusion may be used. For example, the CLONTECH™ pHcRed1-Nuc vector, when transfected into a cell line in accordance with the present invention, produces a red fluorescence signal in the nucleus. Other known fluorescent markers can be used to mark other areas, such as the cell cytoplasm, in a different color channel.

Figure 10:
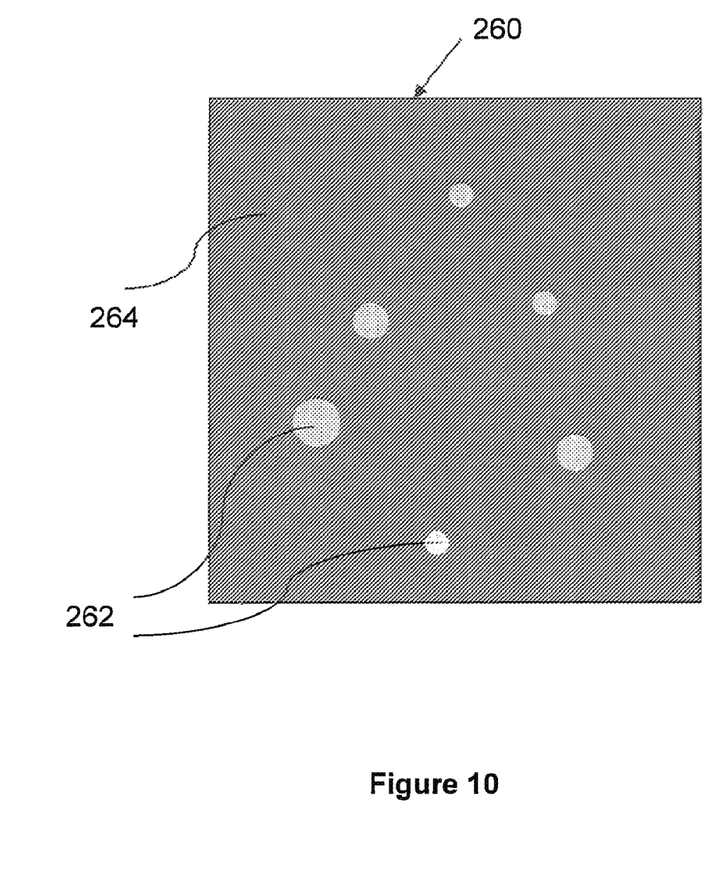
FIG. 10 shows schematically an image of biological object components recorded in accordance with an embodiment of the invention.

Referring now to FIG. 10, in one such embodiment the imaging system additionally records, in addition to the image recorded in accordance with previous embodiments, a second image 260 of the cells and the environment across the imaging area in a second channel of the imaging system. The second CEA provides a contrast between relatively light areas 262 of the second image which corresponds to cell nuclei of the cells and relatively dark areas 264 corresponding to areas surrounding the cell nuclei which include the cell cytoplasm and the medium. These two recorded images are co-registered such that the pixels of each image are aligned. This is saved in a file known as an image stack. An image stack is a collection of images that logically belong together for analysis purposes. In most cases, a given image stack will contain images that share a common acquisition.

Figure 11:
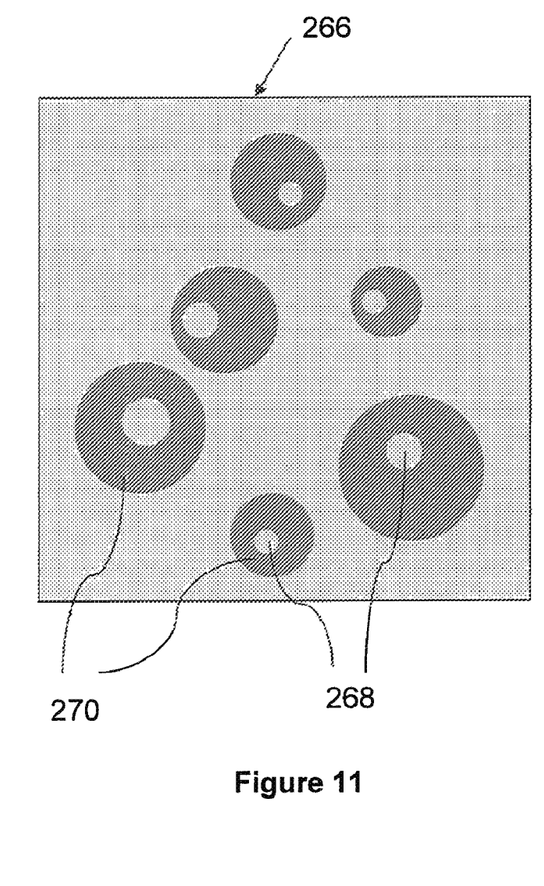
FIG. 11 shows schematically an image of biological objects and biological object components recorded in accordance with an embodiment of the invention.

Referring now to FIG. 11, in a different embodiment an image 266 is recorded which is similar to the image of the cells and the environment recorded using the confocal microscope in accordance with previous embodiments, but which also includes images of the sub-cellular components. The second CEA provides a contrast between relatively light areas 268 of the image which correspond to the cell nuclei and relatively dark areas 270 corresponding to the cell cytoplasm. Recording one image having images of the cells and the components requires the use of only one channel, rather than two channels, of the imaging system. The channel which is therefore unused may be used to detect different characteristics of the cells and the medium across the imaging area. Further channels of the imaging system may be used to image further different characteristics of the cell culture and these different images may be co-registered with the other images to form an image stack.

The contrast provided by the second CEA in the second image 260 or the image 266 including the images of the sub-cellular components and the cells allows a spatial definition for one or more of the components to be derived, as will be described later.

In further embodiments of the present invention, the CEA and/or the second CEA may alternatively emit radiation of a different wavelength or emit a different type of radiation, for example luminescent radiation such as chemiluminescence and phosphorescence. Dimensions of the sample wells, the location of the plane of the imaging area and the chemical compound of the material, the CEA, the second CEA and the medium may be different to those described above. The medium as described previously is a non-biological medium, however, in different embodiments, the medium may instead be biological.

Image Processing and Analysis

A spatial definition is derivable for the cells in any one of the images recorded previously by analysing the image using the image processing and analysis software system according to a number of steps. The image analysis may be fully automated, or controlled by way of settings modified by a user via a graphical user interface provided by the image analysis software system.

Figure 12:
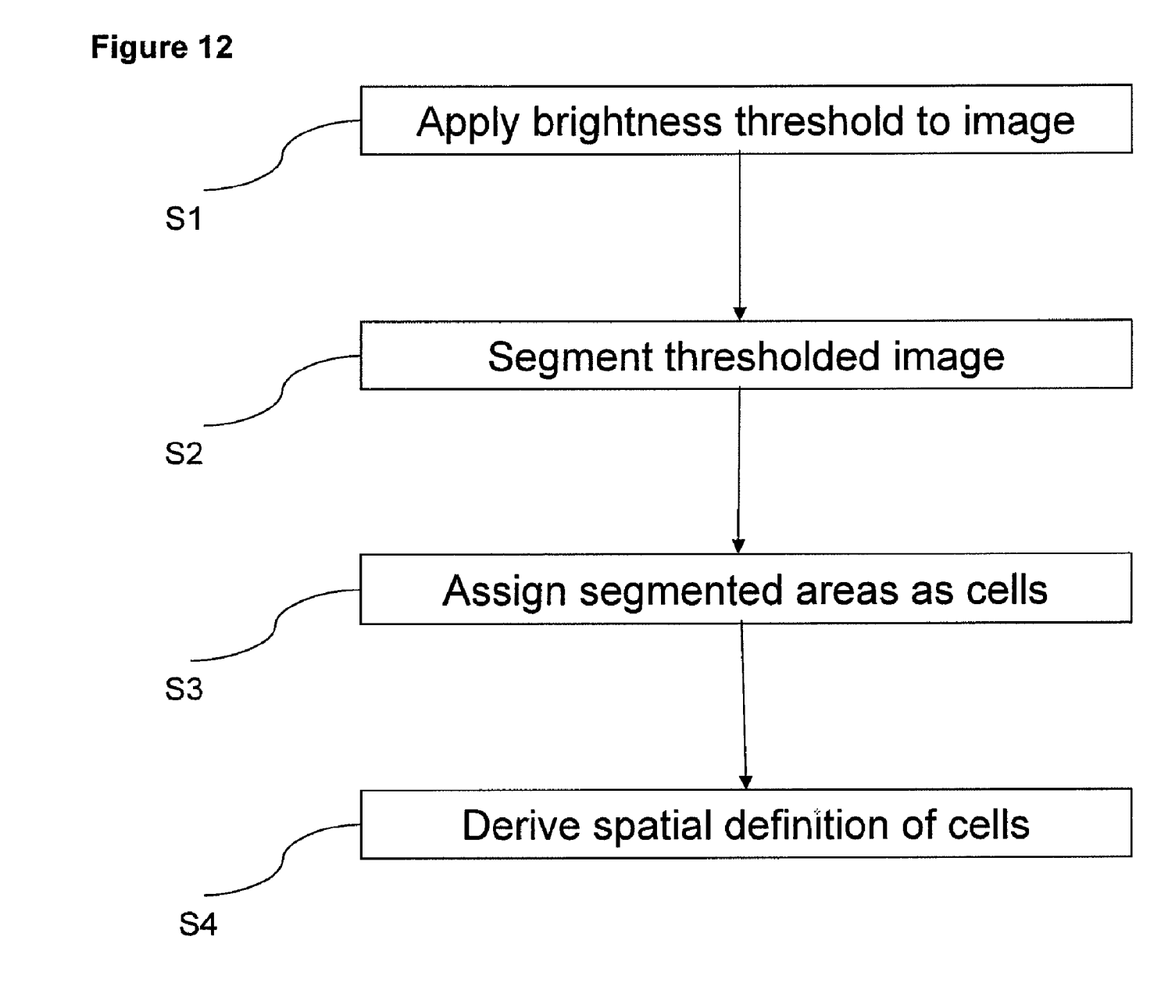
FIG. 12 is a flow diagram of steps for deriving a spatial definition in accordance with an embodiment of the present invention.
Figure 13:
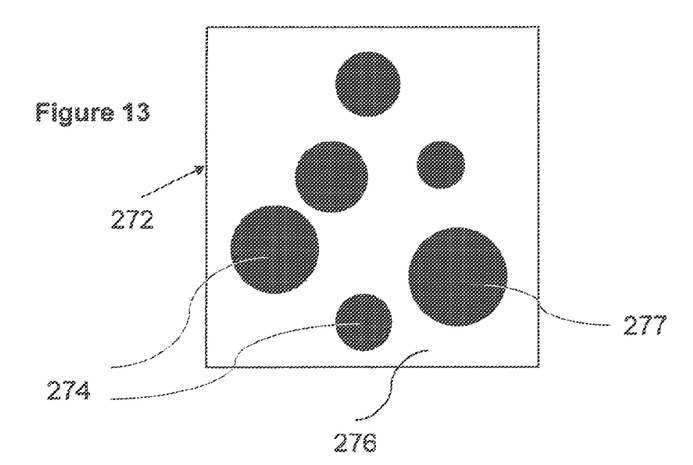
FIG. 13 shows schematically a thresholded image of biological objects in accordance with an embodiment of the present invention.

Reference is made to FIG. 12 which details the steps of the image analysis. These steps will be described below in respect of the image 240 recorded in the embodiment described with reference to FIG. 5. A brightness threshold is applied S1 to the recorded image 240 in order to identify relatively dark pixels and relatively light pixels of the image. The level of the brightness threshold is set on the basis of areas of the image having different brightness intensities which are provided by the CEA. FIG. 13 shows a thresholded image 272 of the image 240. Application of the threshold produces the thresholded image 272 which has both areas of relatively dark pixels 274 which correspond with pixels of the recorded image 240 having a brightness intensity below the threshold and areas of relatively light pixels 276 having a brightness intensity above the threshold. One area 277 of relatively dark pixels corresponds to one of the cells.

The thresholded image 272 is then segmented S2 into segmented object areas. Each object area corresponds to an area of the thresholded image 272 which corresponds to one cell. The segmentation is performed by a segmentation algorithm such as a gray scale segmentation algorithm, a granular segmentation algorithm a binary segmentation algorithm, or a multi-scalar segmentation algorithm.

The segmented object areas are next assigned S3 as cells, and regions outside of these segmented areas are assigned as the medium. For the previously described embodiments where the CEA emits radiation, relatively dark object areas of the image are separated out and assigned as the cells. For the previously described embodiment where the CEA is opaque to transmitted radiation, relatively light object areas of the thresholded image are separated out and assigned as the cells.

Figure 14:
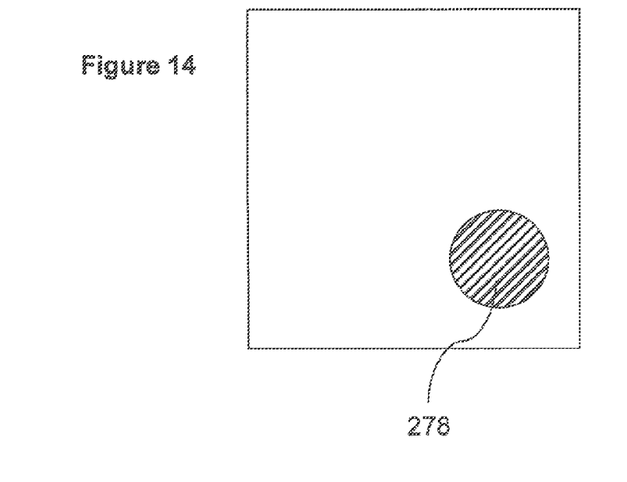
FIG. 14 shows schematically a spatial definition of a biological object in accordance with an embodiment of the invention.

Following this, a spatial definition is derived S4 for each of the segmented object areas of the image corresponding to the cells. FIG. 14 shows schematically a spatial definition 278 derived for the one area 277 of the thresholded image 272 corresponding to the one cell. Each spatial definition identifies pixels within the recorded image 240 in order to define an image area which corresponds to one of the cells.

Figure 15:
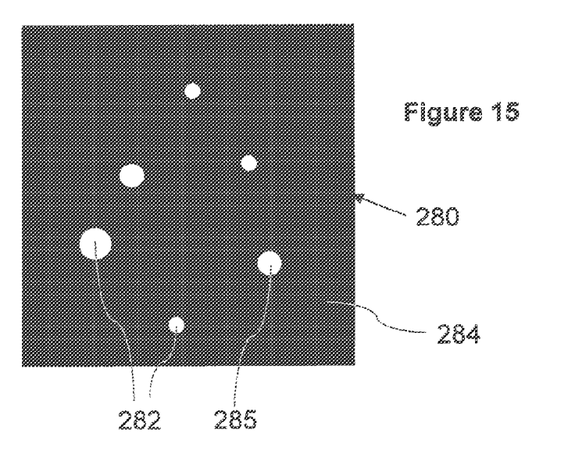
FIG. 15 shows schematically a thresholded image of biological object components in accordance with an embodiment of the invention.
Figure 16:
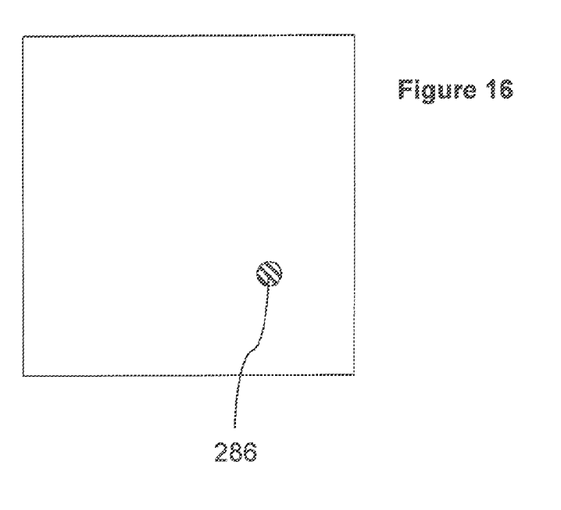
FIG. 16 shows schematically a spatial definition of a biological object component in accordance with an embodiment of the invention.

A similar image analysis is used for the recorded images having a contrast provided by the second CEA. FIG. 15 shows schematically a thresholded image 280 produced by application of the brightness threshold to the second recorded image 260 described with reference to FIG. 10. Areas of relatively light pixels 282 correspond to the cell nuclei and areas of relatively dark pixels 284 correspond to the areas surrounding the cell nuclei. One area 285 of relatively light pixels corresponds to one of the cell nuclei. The thresholded image 280 is then segmented into object component areas which correspond to the sub-cellular components. Each object component area corresponds to one of the cell nuclei. Each object component area is assigned as a cell nucleus and a spatial definition for each cell nucleus is derived. FIG. 16 shows schematically a spatial definition 286 derived for the one area 285 of the thresholded image 280 corresponding to the one cell nucleus.

For the embodiment described with reference to FIG. 11, the recorded image 266 is similarly thresholded. Areas of relatively light pixels of this thresholded image correspond to the cell nuclei and the medium, and areas of relatively dark pixels correspond to the cell cytoplasm. The thresholded image is then segmented into object areas and object component areas which are subsequently assigned as cells and cell nuclei, respectively. Spatial definitions for the cells and the cell nuclei are then derived.

Prior to segmenting the image, pre-processing algorithms may be applied to the image, such as flat field correction, de-noising and de-shading. Post-processing algorithms may also be applied before segmentation, including sieving, object de-clumping, tessellation, and erosion or dilation of the segmented image objects.

Figure 17:
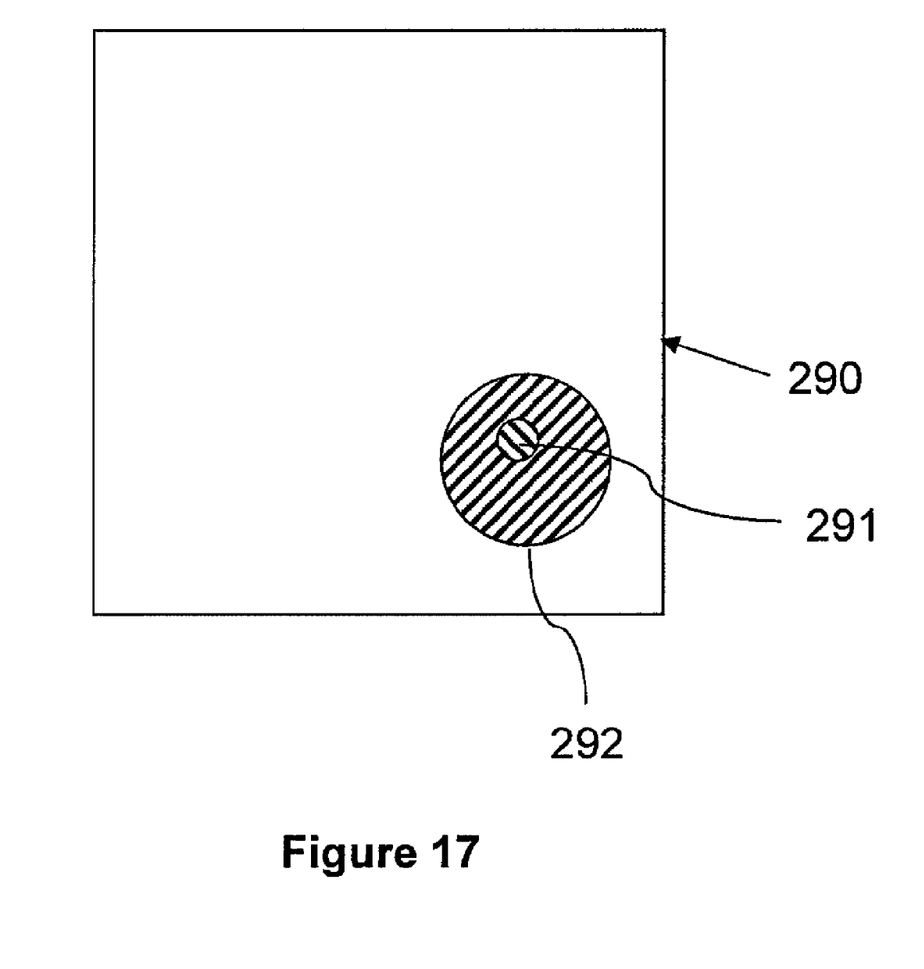
FIG. 17 shows schematically a mask in accordance with an embodiment of the invention.

The derived spatial definitions may be used to process the recorded images of the cells further. Additionally, further recorded images of the cells, which are recorded in one, or in multiple channels of the imaging system, may also be processed using the derived spatial definitions. In one example, the derived spatial definitions may be used to form an image mask. FIG. 17 shows schematically a mask 290 having both a nuclear mask 291 corresponding to the spatial definition 286 of the one cell nucleus referred to in FIG. 16 and a cytoplasmic mask 292 corresponding to the spatial definition 278 of the one cell referred to in FIG. 14, but without the spatial definition 286 of the one cell nucleus. A cell mask of the one cell comprises both the cytoplasmic mask 292 and the nucleus mask 291 together. Such masks may be used to process further recorded images of the cell culture, recorded in one, or in many, channels. For example, the masks may be used to spatially define regions of such further images which correspond to the cells, cell cytoplasm and/or cell nucleus.

Figure 18A:
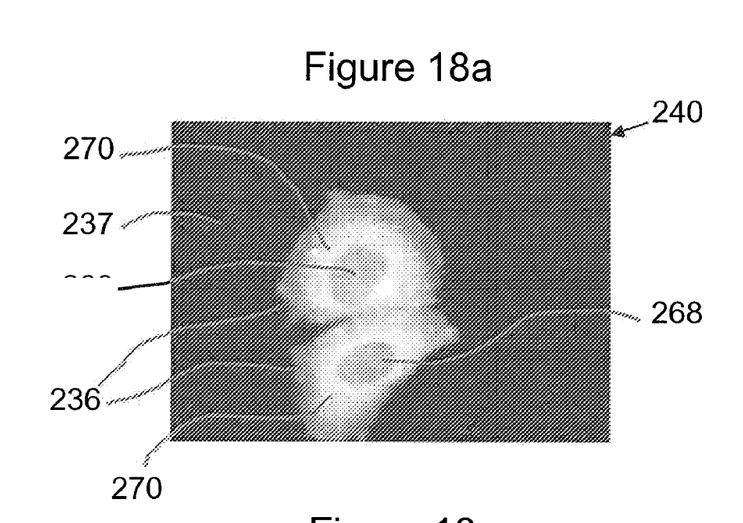
FIGS. 18A, 18B, 18C and 18D show an exemplary image of biological objects recorded and imaged in accordance with an embodiment of the invention.
Figure 18B:
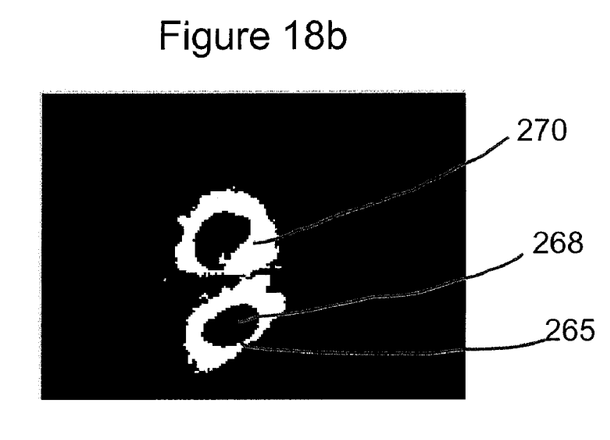
Figure 18C:
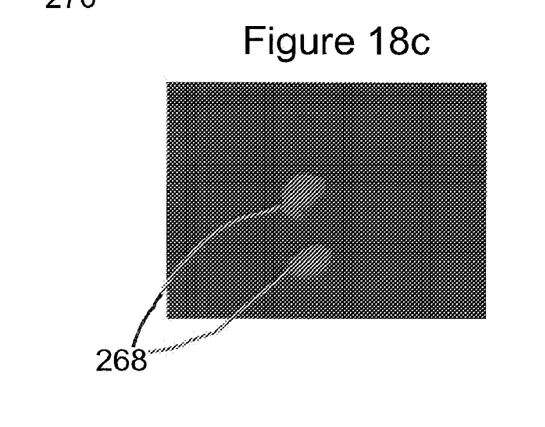
Figure 18D:
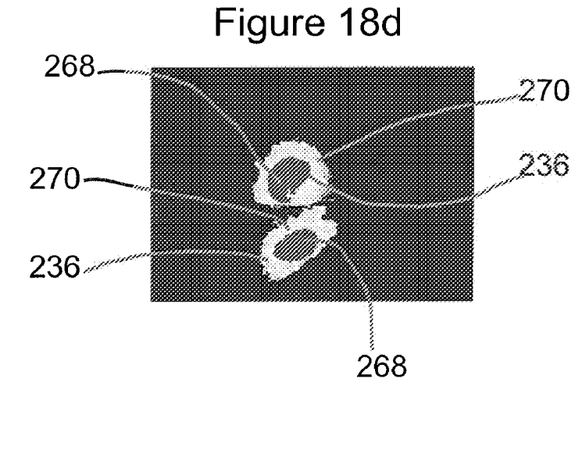

FIG. 18A shows an image 240 of two CHO cells 236 which are expressing Green Fluorescence Protein (GFP), in particular EGFP (BD Clontech). Other forms of fluorescent proteins are known such as Emerald (Tsien, Annu Revs. Biochem., (1998), 67, 509-544) or J-Red (Evrogen). The GFP is localized in the cytoplasm 270 and provides contrast with the relatively dark area of the nucleus 268 and the excluded medium 237. The fluorescent cytoplasmic protein is identified following thresholding as shown by the white region 270 of the bitmap overlay in FIG. 18B. From this information, an inner perimeter 265 around the nucleus 268 can be identified computationally (e.g. pixels within the perimeter are given a value of 1, while pixels outside of the perimeter are given a value of 0) to create a nuclear 'mask', FIG. 18C. Note that in this example, the perimeter may be defined by means of the light area of the cytoplasm. The nuclear mask created has dimensions (e.g. area, diameter, perimeter, centre etc) that can be reported. The mask can now be used to interrogate a nuclear source image so that nuclear measurements (such as intensity) can be acquired. FIG. 18D shows the nuclear bitmap superimposed on the cytoplasmic 270 source image, and demonstrates that the nuclear bitmap accurately identifies the nuclear region 268 of each cell.

The skilled person will appreciate that once a particular mask has been produced from a first source image it can be used to interrogate a second source image. For example, fluorescent probes are known which can move between the cytoplasm and the nucleus in response to a particular drug (e.g. 'Ad-A-gene vectors, Amersham Biosciences; GFP Assays: Live-Cell Translocation Assays, Amersham Biosciences); by using the nuclear mask from the first source image it is possible to interrogate the probe in a second source image and quantify the amount of probe in the nuclear region.

The present invention is useful for identifying pharmacological agents for the treatment of disease. It provides a potentially automated, high throughput method of conducting a wide variety of biological assays where it is important that compounds used to identify the biological objects and/or components of the objects do not cause a deterioration of the health of the cell culture during the time period of the assay. Such assays can be conducted on chemical compounds or any molecule of biological interest, including but not limited to drug candidates, such as those found in combinatorial libraries, allowing high throughput screening of chemical compounds of biological interest.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A method of imaging one or more biological objects using imaging apparatus capable of capturing an image across an imaging area, said method including:
   a) placing said one or more biological objects in an environment;
   b) providing a contrast enhancing agent which provides contrast in an image between said one or more biological objects and said environment;
   c) recording an image of said one or more biological objects and said environment using said imaging apparatus which recording step comprises transmitting radiation through said environment and detecting said transmitted radiation; and
   d) deriving a spatial definition for said one or more biological objects using contrast in said image which is provided by said contrast enhancing agent,
   wherein said contrast enhancing agent is provided in step b) in said environment which is outside of said one or more biological objects, further wherein said contrast enhancing agent is provided in a medium in which said one or more biological objects are supported.

2. The method of claim 1, wherein said contrast enhancing agent is provided in a medium in which said one or more biological objects are supported.

3. The method of claim 2, comprising transmitting radiation through said environment and detecting said transmitted radiation during said recording in step c).

4. The method of claim 3, comprising arranging said contrast enhancing agent with a transmissivity for said transmitted radiation which is lower than a transmissivity of said one or more biological objects for said transmitted radiation.

5. The method of claim 4, comprising separating out relatively light areas of said image and assigning said relatively light areas as said one or more biological objects.

6. The method of claim 2, comprising arranging said agent to emit radiation and, during said recording in step c), detecting the emitted radiation.

7. The method of claim 6, comprising separating out relatively dark areas of said image and assigning said relatively dark areas as said one or more biological objects.

8. The method of claim 1, comprising providing a medium in which said one or more biological objects are supported and providing said contrast enhancing agent in a region outside of said medium.

9. The method of claim 8, comprising providing a receptacle containing said one or more biological objects, wherein at least part of said receptacle is formed of said contrast enhancing agent.

10. The method of claim 8, comprising providing a receptacle containing said one or more biological objects, wherein an inside surface of said receptacle includes a coating which includes a layer of said contrast enhancing agent.

11. The method of claim 10, comprising rendering said coating adhesive, such that said one or more biological objects adhere to a surface of said coating.

12. The method of claim 8, comprising arranging said agent to emit radiation and, during said recording in step c), detecting the emitted radiation.

13. The method of claim 12, comprising arranging said contrast enhancing agent such that said one or more biological objects restrict or prevent a presence within said one or more objects of said emitted radiation which is available for detection.

14. The method of claim 8, comprising separating out relatively dark areas of said image and assigning said relatively dark areas as said one or more biological objects.

15. The method of claim 1, further comprising:
   i) applying a brightness threshold to said image in order to identify relatively dark pixels and relatively light pixels, so as to produce a thresholded image;
   ii) segmenting said thresholded image into object areas.

16. The method of claim 1, wherein said spatial definition identifies pixels within said image.

17. The method of claim 1, wherein said one or more biological objects include one or more components within said one or more objects and said method comprises marking said components with a second contrast enhancing agent which provides contrast in an image between said components and other areas of said one or more biological objects.

18. The method of claim 17, comprising recording a second image of said one or more biological objects and said environment using said imaging apparatus, whereby a spatial definition for one or more of said components is derivable using contrast in said second image which is provided by said second contrast enhancing agent.

19. The method of claim 17, whereby a spatial definition for one or more of said components is derivable using contrast in said image recorded in step c) which is provided by said second contrast enhancing agent.

20. The method of claim 1, wherein said contrast enhancing agent is a biological or a non-biological material.

21. The method of claim 1, wherein said contrast enhancing agent is a fluorescent protein or a dye.

22. The method of claim 1, wherein said contrast enhancing agent is non-toxic to said one or more biological objects.

23. The method of claim 1, wherein said one or more biological objects are cells.

* * * * *